United States Patent
Puckette et al.

(10) Patent No.: US 7,615,671 B2
(45) Date of Patent: Nov. 10, 2009

(54) HYDROGENATION PROCESS FOR THE PREPARATION OF 1,2-DIOLS

(75) Inventors: Thomas Allen Puckette, Longview, TX (US); Kenneth Wayne Hampton, Jr., Gladewater, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/274,787

(22) Filed: Nov. 20, 2008

(65) Prior Publication Data

US 2009/0143612 A1 Jun. 4, 2009

Related U.S. Application Data

(60) Provisional application No. 60/991,529, filed on Nov. 30, 2007.

(51) Int. Cl.
C07C 29/149 (2006.01)
C07C 29/141 (2006.01)
C07C 29/145 (2006.01)

(52) U.S. Cl. .................. 568/864; 568/862; 568/863

(58) Field of Classification Search .............. 568/864, 568/862, 863
See application file for complete search history.

(56) References Cited

U.S. PATENT DOCUMENTS

| | | | |
|---|---|---|---|
| 2,607,805 A | 8/1952 | Gresham | |
| 3,260,759 A | 7/1966 | Skinner | |
| 4,088,682 A | 5/1978 | Jordan | |
| 4,112,245 A | 9/1978 | Zehner et al. | |
| 4,200,765 A | 4/1980 | Goetz | |
| 4,214,106 A | 7/1980 | Freudenberger et al. | |
| 4,232,170 A | 11/1980 | Grey et al. | |
| 4,317,918 A | 3/1982 | Takano et al. | |
| 4,317,946 A | 3/1982 | Costa | |
| 4,321,414 A | 3/1982 | Costa | |
| 4,382,148 A | 5/1983 | Drent | |
| 4,409,395 A | 10/1983 | Miyazaki et al. | |
| 4,418,227 A | 11/1983 | Pez et al. | |
| 4,443,639 A | 4/1984 | Pesa et al. | |
| 4,480,115 A | 10/1984 | McGinnis | |
| 4,496,781 A | 1/1985 | Jacobson et al. | |
| 4,611,085 A | 9/1986 | Kitson | |
| 4,777,302 A | 10/1988 | Haji et al. | |
| 4,777,303 A | 10/1988 | Kitson et al. | |
| 4,870,208 A | 9/1989 | Chan et al. | |
| 4,997,978 A | 3/1991 | Gauthier-Lafaye et al. | |
| 5,077,442 A | 12/1991 | Hara et al. | |
| 5,763,688 A | 6/1998 | Ikariya et al. | |
| 5,841,003 A | 11/1998 | Slaugh et al. | |
| 6,184,413 B1 | 2/2001 | Davis et al. | |
| 6,215,030 B1 | 4/2001 | Morikawa et al. | |
| 6,469,222 B2 | 10/2002 | Knifton et al. | |
| 6,495,730 B1 | 12/2002 | Konishi et al. | |
| 6,720,439 B1 | 4/2004 | Ohkuma et al. | |
| 6,878,852 B2 | 4/2005 | Rautenstrauch et al. | |
| 6,906,228 B2 | 6/2005 | Fischer et al. | |
| 6,939,981 B1 | 9/2005 | Boaz | |
| 7,208,643 B2 | 4/2007 | Namba et al. | |
| 2004/0063966 A1 | 4/2004 | Rautenstrauch et al. | |
| 2005/0234269 A1 | 10/2005 | Kilner et al. | |
| 2005/0245748 A9 | 11/2005 | Rautenstrauch et al. | |
| 2007/0123739 A1 | 5/2007 | Crabtree et al. | |
| 2007/0142679 A1 | 6/2007 | Wood et al. | |

FOREIGN PATENT DOCUMENTS

| | | |
|---|---|---|
| JP | 1983013527 A | 1/1983 |
| JP | 2004300130 A | 10/2004 |
| JP | 2004300131 A | 10/2004 |
| JP | 2005112737 A | 4/2005 |
| WO | WO 03/093208 A1 | 11/2003 |
| WO | WO 2005/051874 A1 | 6/2005 |
| WO | WO 2005051907 A1 | 6/2005 |
| WO | WO 2008035123 A2 | 3/2008 |

OTHER PUBLICATIONS

Barbaro et al. "Hydrogenation of Indole by Phosphone-Modified Rhodium and Ruthenium Catalysts," *Organometallics* 2002, 21, pp. 1430-1437.

Boxwell et al. "A Highly Selective Arene Hydrogenation Catalyst that Operates in Ionic Liquid," *J. Am. Chem. Soc.* 2002, 124, pp. 9334-9335.

Teunissen et al. "Ruthenium catalysed hydrogenation of dimethyl oxalate to ethylene glycol," *Chem. Commun.*, 1997, pp. 667-668.

(Continued)

*Primary Examiner*—Elvis O Price
(74) *Attorney, Agent, or Firm*—Eric D. Middlemas; Bernard J. Graves, Jr.

(57) ABSTRACT

Disclosed is a process for the preparation of 1,2-glycols by hydrogenation of 1,2-dioxygenated organic compounds in the presence of a catalyst composition comprising a ruthenium compound, a trivalent phosphorus compound selected from 1,1,1-tris(diarylphosphinomethyl)alkyl or substituted alkyl, and a promoter selected from Lewis acids, protic acids having an ionization constant ($K_i$) of $5 \times 10^{-3}$ or greater, and onium salts. The process is useful for the hydrogenation of glycolic acid or derivatives thereof to ethylene glycol.

15 Claims, No Drawings

OTHER PUBLICATIONS

Boardman et al. "A tripodal sulfur ligand for the selective ruthenium-catalysed hydrogenation of dimethyl oxalate," *Chem. Commun.*, 2006, pp. 2289-2291.

J. E. Carnahan et al. "Ruthenium-catalyzed Hydrogenation of Acids to Alcohols," *J. Am. Chem. Soc.* 1955, 77, pp. 3766-3768.

Fahey, Darryl R., "Rational Mechanism for Homogeneous Hydrogenation of Carbon Monoxide to Alcohols, Polyols, and Esters," *J. Am. Chem. Soc.* 1981, 103, pp. 136-141.

Matteoli et al. Homogeneous Catalytic Hydrogenation of Dicarboxylic Acid Esters, *Journal of Molecular Catalysis*, 22 (1984) pp. 353-362.

Matteoli et al. "Homogeneous Catalytic Hydrogenation of the Esters of Bicarboxylic Acids, Part III, Ethylene Glycol from Dimethyl Oxalate," *Journal of Molecular Catalysis*, 44 (1988) pp. 347-355.

Matteoli et al. "Selective reduction of dimethyl oxalate by ruthenium carbonyl carboxylates in homogeneous phase Part IV," *Journal of Molecular Catalysis*, 64 (1991) pp. 257-267.

Nomura et al. "Direct synthesis of 2-phenylethanol by hydrogenation of methyl phenylacetate using homogeneous ruthenium-phosphine catalysis under low hydrogen pressure," *Journal of Molecular Catalysis A: Chemical* 166 (2001) pp. 345-349.

Matteoli et al. "Homogeneous Catalytic Hydrogenation of Dicarboxylic Acid Esters II," *Journal of Organometallic Chemistry*, 299 (1986) pp. 233-238.

Matteoli et al. "Structure and catalytic activity of phosphine-substituted ruthenium carbonyl carboxylates," *Journal of Organometallic Chemistry* 498 (1995) pp. 177-186.

Knifton, John F., "Syngas Reactions Part XIII. The Ruthenium 'Melt'-Catalyzed Oxonation of Terminal Olefins," *Journal of Molecular Catalysis*, 47 (1988) pp. 99-116.

Nomura et al. "Ruthenium catalyzed hydrogenation of methyl phenylacetate under low hydrogen pressure," *Journal of Molecular Catalysis A., Chemical* 178 (2002) pp. 105-114.

Sung et al. "Syntheses of ruthenium(II) complexes containing polyphosphine ligands and their applications in the homogeneous hydrogenation," *Polyhedron* 18 (1999) pp. 469-479.

Teunissen et al. "Homogeneous ruthenium catalyzed hydrogenation of esters to alcohols," *Chem. Commun.*, 1998, pp. 1367-1368.

Satchell et al. "Quantitative Aspects of the Lewis Acidity of Covalent Metal Halides and Their Organo Derivatives," *Chemical Reviews*, vol. 69, No. 3, Jun. 1969, pp. 251-278.

Hara et al. "Selective Hydrogenation of Cyclic Ester to $\alpha$, $\omega$-Diol Catalyzed by Cationic Ruthenium Complexes with Trialkylphosphine Ligands," *Chemistry Letters*, 1992, pp. 1983-1986.

Grey et al. "Homogeneous Catalytic Hydrogenation of Carboxylic Acid Esters to Alcohols," *J.C.S. Chem. Comm.*, 1980, pp. 783-784.

van Engelen et al. "Suitable ligands for homogeneous ruthenium-catalyzed hydrogenolysis of esters," *Journal of Molecular Catalysis A: Chemical* 206 (2003) pp. 185-192.

Grey et al. "Anionic Metal Hydride Catalysts. 2. Application to the Hydrogenation of Ketones, Aldehydes, Carboxylic Acid Esters, and Nitriles," *J. Am. Chem. Soc.* 1981, 103, pp. 7536-7542.

International Search Report dated Apr. 21, 2009 in corresponding PCT application PCT/US2008/013085.

HYDROGENATION PROCESS FOR THE PREPARATION OF 1,2-DIOLS

CROSS REFERENCES TO RELATED APPLICATIONS

This application claims the benefit of U.S. Provisional Application Ser. No. 60/991,529, filed Nov. 30, 2007, which is incorporated herein by reference in its entirety.

FIELD OF THE INVENTION

The invention generally relates to a process for hydrogenation of 1,2-dioxygenated organic compounds using a promoted ruthenium-based catalyst system to produce their corresponding 1,2-diols. More specifically, this invention relates to a process for the preparation of 1,2-diols by hydrogenation of 1,2-dioxygenated organic compounds using a ruthenium catalyst system comprising 1,1,1-tris(diarylphos-phinomethyl)alkyl and a promoter.

BACKGROUND OF THE INVENTION

The complete reduction of 1,2-dioxygenated organic compounds to their corresponding 1,2-diols such as, for example, glycolic acid to ethylene glycol, has historically proven to be difficult. For example, the reduction of oxalate esters typically yields glycolate esters, and glycolate esters are often only slightly reactive. Ethylene glycol production is very slow and often requires extended reaction times.

Thus, there is a need in the art for processes to effectively and efficiently hydrogenate 1,2-dioxygenated organic compounds to their corresponding 1,2-diols. In particular, there is a need for processes that show high reaction rates with good reaction selectivity. The present invention addresses this need as well as others that will be apparent to those skilled in the art upon reading the remaining description and the appended claims.

SUMMARY OF THE INVENTION

We have found that the hydrogenation of 1,2-dioxygenated organic compounds can be carried out efficiently in the presence of a ruthenium catalyst system comprising 1,1,1-tris(diarylphosphinomethyl)alkyl and a promoter. Thus, in a general embodiment, the invention provides a process for preparing a 1,2-diol, comprising contacting a 1,2-dioxygenated organic compound, with the exception of oxalic acid or ester thereof, with hydrogen, under hydrogenation conditions, in the presence of a catalyst composition comprising:
  (a) a ruthenium compound;
  (b) a trivalent phosphorus compound selected from 1,1,1-tris(diarylphosphinomethyl)alkyl or substituted alkyl; and
  (c) a promoter selected from Lewis acids, protic acids having an ionization constant ($K_i$) of $5 \times 10^{-3}$ or greater, onium salts, and mixtures thereof;
  wherein the catalyst components (a)-(c) are dissolved in an organic solvent, to produce a 1,2-diol.

In another embodiment, the process may be used for preparing ethylene glycol. The process comprises contacting glycolic acid or a derivative thereof with hydrogen, under hydrogenation conditions, in the presence of a catalyst composition comprising:
  (a) ruthenium(III)acetylacetonate;
  (b) 1,1,1-tris(diphenylphosphinomethyl)ethane; and
  (c) a promoter selected from tetrabutylammonium hexafluorophosphate, triflic acid, toluenesulfonic acid, dodecylbenzenesulfonic acid, dinonylnaphthalene-sulfonic acid, and mixtures thereof;
  wherein the catalyst components (a)-(c) are dissolved in a solvent selected from methanol, ethylene glycol, 2-methyl-1,3-propanediol, 2-ethylhexanol, hexanol, octanol, and mixtures thereof; to produce ethylene glycol.

DETAILED DESCRIPTION OF THE INVENTION

We have found that the reduction of 1,2-dioxygenated organic compounds, such as glycolic acid and glycolate esters to ethylene glycol, is facile with the correct combination of reaction conditions, phosphorus and ruthenium components, promoter, and solvent. In particular, it has been discovered that a ruthenium-based catalyst system is effective for the reduction of 1,2-dioxygenated organic compounds to their corresponding 1,2-diols. The catalyst of the present invention overcomes the sluggish catalyst activity reported by others and gives high yields and high selectivity to 1,2-diols.

One aspect of the invention, therefore, is a process for preparing a 1,2-diol, comprising contacting a 1,2-dioxygenated organic compound, with the exception of oxalic acid or ester thereof, with hydrogen, under hydrogenation conditions, in the presence of a catalyst composition comprising:
  (a) a ruthenium compound;
  (b) a trivalent phosphorus compound selected from 1,1,1-tris(diarylphosphinomethyl)alkyl or substituted alkyl; and
  (c) a promoter selected from Lewis acids, protic acids having an ionization constant ($K_i$) of $5 \times 10^{-3}$ or greater, onium salts, and mixtures thereof;
  wherein the catalyst components (a)-(c) are dissolved in an organic solvent, to produce a 1,2-diol.

The process comprises contacting a 1,2-dioxygenated organic compound, with the exception of oxalic acid or ester thereof, with hydrogen, under hydrogenation conditions, in the presence of the catalyst composition described herein. The term "1,2-dioxygenated organic compound", as used herein, is intended to mean an organic compound in which adjacent carbon atoms are bonded to one or more, different oxygen atoms and in which there is a double bond between at least one of the adjacent carbon atoms and its oxygen substituent. For example, the adjacent carbon atoms each may be part of an aldehyde, keto, carbonyloxy, ester, or hydroxyl group as long as one of them has a double bond to an oxygen atom. Representative classes of 1,2-dioxygenated organic compounds include, but are not limited to, α-hydroxyalkanoic acids and esters thereof, α-hydroxyketones and aldehydes, α-ketocarboxylic acids and esters thereof, and α-diketones. The term "esters thereof", in the context of the above list of compounds, means an ester formed by the reaction of a carboxylic acid with the hydroxy group, by the reaction of alcohols with the carboxylic acid group, or a combination thereof, and polymeric or oligomeric esters formed by the condensation of 2 or more α-hydroxyalkanoic acid molecules.

Examples of 1,2-dioxygenated organic compounds suitable for hydrogenation in the process of the invention include glyoxal, glycolic acid, glycol aldehyde, glycol aldehyde dimer, glycolic acid esters, methyl glycolate, oligomers of glycolic acid, oligomers of glycolic acid esters, lactic acid, lactic acid esters, oligomers of lactic acid, oligomers of lactic acid esters, 2-hydroxy butyric acid, esters of 2-hydroxy butyric acid, oligomers of 2-hydroxy butyric acid, and mixtures thereof. In another example, the 1,2-dioxygenated organic compound comprises glycolic acid, esters of glycolic acid, oligomers of glycolic acid, oligomers of glycolic acid esters, or mixtures thereof. In yet another example, the 1,2-dioxygenated organic compound comprises glycolic acid, esters of glycolic acid, or mixtures thereof. Excluded from the present invention are embodiments in which the 1,2-dioxygenated organic compound comprises oxalic acid, esters of oxalic acid, or mixtures thereof.

Our hydrogenation process produces 1,2-diols corresponding to the 1,2-dioxygenated organic compound starting material. Particularly desirable 1,2-diols that the process of the invention can produce include ethylene glycol, 1,2-propylene glycol, 1,2-butanediol, or a mixture thereof. Thus, for example, ethylene glycol can be produced from glyoxal, glycolic acid, glycol aldehyde, glycol aldehyde dimer, glycolic acid esters, methyl glycolate, oligomers of glycolic acid, oligomers of glycolic acid ester or mixtures thereof; 1,2-propylene glycol can be produced from lactic acid, lactic acid esters, oligomers of lactic acid, oligomers of lactic acid ester or mixtures thereof; and 1,2-butanediol can be produced from 2-hydroxy butyric acid, esters of 2-hydroxy butyric acid, oligomers of 2-hydroxy butyric acid, or mixtures thereof. In one embodiment, for example, the 1,2-dioxygenated organic compound comprises glycolic acid, an ester of glycolic acid, oligomers thereof, or mixtures thereof and the 1,2-diol product comprises ethylene glycol. In another example, the 1,2-dioxygenated organic compound comprises lactic acid, lactic acid esters, oligomers of lactic acid, oligomers of lactic acid esters or mixtures thereof, and the 1,2-diol comprises 1,2-propylene glycol.

The ruthenium compound is not particularly limiting. It can be any ruthenium source that is soluble in an organic solvent. Example compounds include ruthenium salts, hydride complexes, carbonyl compounds, halides, oxides, phosphine complexes, and mixtures thereof. Suitable ruthenium salts include ruthenium carboxylates and acetylacetonates. For example, the ruthenium compound can comprise the acetonylacetonate complex of ruthenium(III).

The trivalent phosphorus compound is selected from 1,1,1-tris(diarylphosphinomethyl)alkyl and substituted alkyl. The alkyl substituent can have 1 to 40 carbon atoms. Some representative examples of alkyl groups are methyl, ethyl, propyl, butyl, pentyl, isobuty, isopropyl, isopentyl, and the like. The alkyl group can be substituted with any group that does not interfere with the hydrogenation reaction such as, for example, hydroxyl, ether, halogen, sulfonic acid, carboxylic acid, and the like. The aryl group of the trivalent phosphorus compound may have from 6 to 20 carbon atoms. Examples of the aryl groups include, but are not limited to, carbocyclic aryl groups such as phenyl, naphthyl, anthracenyl, and substituted derivatives thereof in which one or more substituent groups can replace hydrogen at any carbon position on the aromatic ring(s). Some typical examples of substituent groups include, but are not limited to, one or more groups selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms.

Some representative examples of substituted aryl groups are 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl and the like; a mono- or di(hydroxy)aryl radical such as 4-hydroxyphenyl, 3-hydroxyphenyl, 2,4-dihydroxyphenyl, and the like; a nitroaryl group such as 3- or 4-nitrophenyl; a cyanoaryl group, for example, 4-cyanophenyl; a mono- or di(lower alkyl)aryl radical such as 4-methylphenyl, 2,4-dimethylphenyl, 2-methylnaphthyl, 4-(iso-propyl)phenyl, 4-ethylnaphthyl, 3-(n-propyl)phenyl and the like; a mono- or di(alkoxy) aryl radical, for example, 2,6-dimethoxyphenyl, 4-methoxyphenyl, 3-ethoxyindenyl, 4-(isopropoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl)aryl radical such as 2-(aminomethyl)phenyl, or a mono- or di(methylsulfonylamino)aryl radical such as 3-(methylsulfonylamino)naphthyl. In one embodiment, for example, the trivalent phosphorus compound can be selected from 1,1,1-tris(diphenylphosphinomethyl)alkyl and substituted alkyl. In another example, the ruthenium compound can be selected from ruthenium salts, hydride complexes, carbonyl compounds, halides, oxides, phosphine complexes, and mixtures thereof; and the trivalent phosphorus compound can be selected from 1,1,1-tris(diphenylphosphinomethyl)alkyl and substituted alkyl. A particularly useful trivalent phosphorus compound is 1,1,1-tris(diphenylphosphinomethyl)ethane (also known as TRIPHOS).

The rate of reaction is enhanced by the addition of a promoter selected from Lewis acids, protic acids having an ionization constant $(K_i)$ of $5 \times 10^{-3}$ or greater, and onium salts. The term "Lewis Acid", as used herein, refers to the G. N. Lewis concept of acid-base equilibria as elaborated in *Chemical Reviews*, 69(3), 251 (June 1969). Examples of Lewis acid promoters include sodium tetraphenyl borate and zinc acetonylacetonate.

The onium salt promoters can comprise an anionic component that is derived from a strong acid having an ionization constant $(K_i)$ of $5 \times 10^{-3}$ or greater such as, for example, phosphoric acid, hexafluorophoshoric acid, hydrobromic acid, tetrafluoroboric acid, trifluoroacetic acid, p-toluenesulfonic acid, triflic acid, sulfuric acid, mixtures thereof, and the like. These anions are neutral to weak bases in comparison to anions such as, for example, hydroxides, carbonates, bicarbonates, and carboxylates without electron-withdrawing substituents. In another example, the onium salt promoters can comprise a non-coordinating anion. Some representative, examples of onium salt promoters include ammonium hexafluorophosphate, tetrabutylammonium hexafluorophosphate, tetraphenylphosphonium bromide, ammonium tetrafluoroborate, tetramethyl ammonium tetrafluoroborate, mixtures thereof and the like.

Examples of protic acids having an ionization constant $(K_i)$ of $5 \times 10^{-3}$ or greater include toluenesulfonic acid, phosphoric acid, triflic acid, sulfuric acid, methanesulfonic acid, trifluoroacetic acid, dodecylbenzenesulfonic acid, dinonylnaphthalenesulfonic acid, and the like. Particularly suitable promoters include tetrabutylammonium hexafluorophosphate, triflic acid, toluenesulfonic acid, dodecylbenzenesulfonic acid, dinonylnaphthalenesulfonic acid, and mixtures thereof. Mixtures of any one of the above Lewis acids, protic acids, and onium salts also may be used.

The organic solvent may be selected from a wide variety of compounds, mixture of compounds, or materials that are liquid at the pressure at which the process is being operated. The main criteria for the solvent are that it can dissolve the catalyst components and reactants, and does not act as a poison to the catalyst. Suitable organic solvents include alcohols, ethers, hydrogenation starting materials, and hydrogenation reaction products. Specific examples of suitable organic solvents include methanol, ethanol, propanol, butanol, isobutanol, isopropanol, ethylene glycol, 1,2-propylene glycol, 1,3-propylene glycol, 2-methyl-1,3-propanediol, neopentyl glycol, 2-ethylhexanol, 1,4-butanediol, diethylene glycol, triethylene glycol, glycerol, hexanol, octanol, methoxy ethanol, diisopropyl ether, dipropyl ether, and mixtures thereof. Particularly suitable solvents include methanol, ethylene glycol, 2-methyl-1,3-propanediol, 2-ethylhexanol, hexanol, octanol, and mixtures thereof.

The concentration of the ruthenium and the trivalent phosphorus ligand in the organic solvent or reaction mixture can vary over a wide range. Typically, a gram mole ligand:gram atom ruthenium ratio of at least 1:1 is maintained in the reaction mixture. More typically, the ratio ranges from 1:1 to 20:1 or 3:1 to 5:1.

The absolute concentration of ruthenium metal in the reaction mixture or solution may vary from 1 mg/liter up to 5000 mg/liter or more. When the process is operated within the practical conditions of this invention, the concentration of ruthenium metal in the reaction solution normally is in the range of about 20 to 600 mg/liter.

The promoter content is usually present in excess of the ruthenium content. The promoter may be present in an amount ranging from 0.5 to 50 molar equivalents. Typically, the promoter is present in an amount ranging from 3 to 50 molar equivalents. The amount of organic solvent used is not particularly limiting. Typically, enough solvent is used to dissolve all of the catalyst components.

No special or unusual techniques are needed for preparing the catalyst systems and solutions of the present invention, although in order to obtain a catalyst of high activity, it is preferred that manipulations of the ruthenium and phosphorus ligand components be carried out under an inert atmosphere, e.g., nitrogen, argon and the like. The desired quantities of a suitable ruthenium compound and ligand can be charged to the reactor in a suitable solvent. The sequence in which the various catalyst components or reactants are charged to the reactor can vary.

Water can be generated during the hydrogenation reaction if the 1,2-dioxygenated starting compound comprises a carboxylic acid. The reaction can tolerate up to about 30% water, by weight of the feed material, either generated in situ or added to the reaction mixture. Typically, however, no water is added to the reaction system. The added water may slow down the reaction rate and make the process less desirable.

Hydrogen pressure has a strong influence on the outcome of the reaction. Lower pressures typically result in a slower rate of reaction. Thus, the most desirable pressure range is in excess of 1500 psig (10.3 MPa). Higher pressure will generally result in a faster rate of reaction, but this is offset by the higher cost of operating at higher pressures. The desirable pressure range will be between 1000 and 5000 psig (6.9-34.5 MPa) with a preferred range of 1500 to 3000 psig (10.3-20.7 MPa).

The process temperature can be varied over a wide range. The desired temperature range can be from 100° C. to 250° C. The more preferable range of temperatures for this process is from 125° C. to 225° C.

The amount of 1,2-dioxygenated organic compound present in the reaction mixture can vary over a wide range. In practice, the rate of reaction is favored by higher concentrations of starting material in the reactor.

Any of the known hydrogenation reactor designs or configurations may be used in carrying out the process provided by the present invention. For example, the process may be conducted in a batchwise manner in an autoclave by contacting the 1,2-dioxygenated organic compound with hydrogen in the presence of the catalyst compositions described herein. It will be apparent to those skilled in the art that other reactor schemes may be used with this invention.

One embodiment of the invention is a process for preparing ethylene glycol, which comprises contacting glyoxal, glycolic acid, glycol aldehyde, glycol aldehyde dimer, glycolic acid ester, methyl glycolate, oligomers of glycolic acid, oligomers of glycolic acid ester or mixtures thereof with hydrogen, under hydrogenation conditions, in the presence of a catalyst composition comprising:

(a) a ruthenium compound;
(b) 1,1,1-tris(diphenylphosphinomethyl)ethane; and
(c) a promoter selected from triflic acid, toluenesulfonic acid, dodecylbenzenesulfonic acid, dinonylnaphthalenesulfonic acid, ammonium hexafluorophosphate, tetrabutylammonium hexafluorophosphate, tetraphenylphosphonium bromide, ammonium tetrafluoroborate, tetramethyl ammonium tetrafluoroborate, and mixtures thereof;

wherein said catalyst components (a)-(c) are dissolved in a solvent selected from methanol, ethylene glycol, 2-methyl-1,3-propanediol, 2-ethylhexanol, hexanol, octanol, and mixtures thereof; to produce ethylene glycol.

The above process is understood to include any combination of the individual promoters, ruthenium compounds, starting glycolic acids and esters, and solvents listed above. For example, the ruthenium compound can comprise ruthenium(III)acetylacetonate. In another example, the ruthenium compound can comprise ruthenium(III)acetylacetonate, the promoter can comprise triflic acid, toluenesulfonic acid, or a mixture thereof, and the solvent can comprise methanol. In yet another example, the promoter can comprise toluenesulfonic acid. In still another example, the ruthenium compound can comprise ruthenium(III)acetylacetonate, the promoter can comprise toluenesulfonic acid, and the solvent can comprise methanol. In still another example, the ruthenium compound can comprise ruthenium(III)acetylacetonate, the promoter can comprise any one of or a mixture of ammonium hexafluorophosphate, tetrabutylammonium hexafluorophosphate, tetraphenylphosphonium bromide, ammonium tetrafluoroborate, and tetramethyl ammonium tetrafluoroborate, and the solvent can comprise methanol. In yet another example, the ruthenium compound can comprise ruthenium (III)acetylacetonate, and the promoter can comprise toluenesulfonic acid, triflic acid, tetrabutylammonium hexafluorophosphate, or a mixture thereof. Yet another embodiment of the invention is a process for preparing ethylene glycol, which comprises contacting glycolic acid or a derivative thereof with hydrogen, under hydrogenation conditions, in the presence of a catalyst composition comprising:

(a) ruthenium(III)acetylacetonate;
(b) 1,1,1-tris(diphenylphosphinomethyl)ethane; and
(c) a promoter selected from tetrabutylammonium hexafluorophosphate, triflic acid, toluenesulfonic acid, dodecylbenzenesulfonic acid, dinonylnaphthalenesulfonic acid, and mixtures thereof;

wherein said catalyst components (a)-(c) are dissolved in a solvent selected from methanol, ethylene glycol, 2-methyl-1,3-propanediol, 2-ethylhexanol, hexanol, octanol, and mixtures thereof; to produce ethylene glycol. In one example, the glycolic acid derivative can comprise methyl glycolate, oligomers of glycolic acid, and mixtures thereof.

The hydrogenation process of the invention may further comprise separating the 1,2-diol product, such as ethylene glycol, from the catalyst components and recycling the catalyst components to the hydrogenation contacting step.

Examples of separation techniques that can be employed to separate the catalyst components from the reaction mixture include vapor stripping, flash distillation, and liquid-liquid extraction. The catalyst, once separated from the product, can be returned to the reactor for reuse. Alternatively, the catalyst solution can be diluted with an alcohol solvent such as methanol or the reaction product such as ethylene glycol and reused. As another alternative, the reaction mixture can be partitioned between an aqueous phase and an organic phase, which will dissolve the catalyst components. The 1,2-diol product can then be recovered from the aqueous phase by simple distillation while the organic phase can be returned to the reactor for reuse. It is understood that the separation process described above can be combined with any of the various embodiments of the inventive process described herein.

This invention can be further illustrated by the following examples of embodiments thereof, although it will be understood that these examples are included merely for purposes of illustration and are not intended to limit the scope of the invention. Unless otherwise indicated, all percentages are by weight.

EXAMPLES

Example 1

Reduction of Methyl Glycolate in Methanol to Ethylene Glycol

The following example shows the positive effect of adding a promoter to the catalyst mixture. Run 1 in the table below is a comparative example. Runs 2-9 represent variants of the current invention.

A 300-milliliter autoclave was charged with Ru(Acac)$_3$ (0.10 mmole), TRIPHOS (0.50 mmole), and the promoter in the amount specified in the table. Methanol (32 milliliters) and methyl glycolate (0.156 mole) were added, and the reactor was sealed under N$_2$. The reactor was pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented, and the contents recovered. The contents were analyzed by the use of an internal standard gas chromatography method for the presence of methyl glycolate ("MG") and ethylene glycol ("EG"). The results are shown in the table below.

| Run | Promoter | Amount of Promoter (mmole) | Conversion of MG (%) | Selectivity to EG (%) | Catalyst Activity Rate (moles EG per mole of Ru per hr) |
|---|---|---|---|---|---|
| 1 | none | none | 39.5 | 88.4 | 205 |
| 2 | Zn Acetonylacetonate | 0.25 | 49.3 | 88.9 | 228 |
| 3 | Me$_4$NBF$_4$ | 0.025 | 99.7 | 98.2 | 509 |
| 4 | Me$_4$NBF$_4$ | 0.001 | 96.8 | 98.2 | 394 |
| 5 | NH$_4$PF$_6$ | 0.025 | 100 | 96.9 | 504 |
| 6 | NH$_4$OAc | 0.150 | 67.8 | 94.8 | 334 |
| 7 | Ph$_4$PBr | 0.025 | 84.1 | 97.8 | 428 |
| 8 | NaPh$_4$B | 0.500 | 81.1 | 93.5 | 394 |
| 9 | BuN$_4$PF$_6$ | 0.025 | 97.8 | 95.8 | 487 |

Analysis of the run without a promoter showed a 39.5% conversion of the methyl glycolate with 88.4% selectivity to ethylene glycol. The catalyst activity rate for this experiment was 205 moles of EG per mole of ruthenium per hour. On the other hand, runs with a promoter showed MG conversions of 49-100%, EG selectivities of 89-98%, and catalyst activity rates of 230-510 moles of EG per mole of ruthenium per hour. This data show the positive effects of adding a promoter to the reaction mixture.

Example 2

Reduction of Methyl Glycolate in Methanol to Ethylene Glycol

A 300-milliliter autoclave was charged with Ru(Acac)$_3$ (0.10 mmole), TRIPHOS (0.50 mmole), and tetrabutylammonium hexafluorophosphate (0.025 mmol). Methanol (32 milliliters) and methyl glycolate (0.156 mole) were added, and the reactor was sealed under N$_2$. The reactor was pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented, and the contents recovered. The contents were analyzed by the use of an internal standard gas chromatography method to show the presence of 0.0034 mole of methyl glycolate and 0.146 mole of ethylene glycol. The catalyst turnover rate for this example is 508 moles of EG per mole of ruthenium per hour.

Example 3

Reduction of Glycolic Acid in Methanol to Ethylene Glycol

A 300-milliliter autoclave was charged with Ru(Acac)$_3$ (0.10 mmole), TRIPHOS (0.50 mmole), and toluenesulfonic acid (0.02 gram). Methanol (32 milliliters) and glycolic acid (0.156 mole) were added, and the reactor was sealed under N$_2$. The reactor was pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented, and the contents recovered. The contents were analyzed by the use of an internal standard gas chromatography method to show the presence of 0.154 mole of ethylene glycol.

Example 4

Reduction of Glycolic Acid in Ethylene Glycol to Ethylene Glycol

A 300-milliliter autoclave was charged with Ru(Acac)$_3$ (0.10 mmole), TRIPHOS (0.50 mmole), and toluenesulfonic acid (0.06 gram). Ethylene glycol (32 milliliters, 0.574 Mole) and glycolic acid (0.156 Mole) were added, and the reactor was sealed under N$_2$. The reactor was pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented, and the contents recovered. The contents were analyzed by the use of an internal standard gas chromatography method to show the presence of 0.744 mole of ethylene glycol. Subtraction of the material charged as solvent (0.547 mole) shows the presence of 0.170 mole of ethylene glycol in the autoclave contents. Measurement errors are suspected to be the reason for greater than 100% accountability. No glycolic acid was detected by gas chromatography.

Example 5

Reduction of Glycolate Oligomers in Methanol to Ethylene Glycol

A 300-milliliter autoclave was charged with Ru(Acac)$_3$ (0.10 mmole), TRIPHOS (0.50 mmole), and toluenesulfonic acid (0.03 gram). Methanol (32 milliliters) and 14.0 grams of a mixture of methyl glycolate and oligomers were added to the autoclave. The glycolate mixture contained 40% methyl glycolate and higher molecular oligomers to give an average molecular weight for the mixture of 150. The reactor was sealed under N$_2$ and then pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented, and the contents recovered. The contents were analyzed by the use of an internal standard gas chromatography method to show the presence of a trace of methyl glycolate and 0.183 mole of ethylene glycol. The catalyst turnover rate for this example is 610 moles of EG per mole of ruthenium per hour.

Example 6

Reduction of Glycolic Acid to Ethylene Glycol With Catalyst Recycle

A 300-milliliter autoclave was charged with Ru(Acac)$_3$ (0.10 mmole), TRIPHOS (0.50 mmole), and toluenesulfonic acid (0.06 gram). Methanol (32 milliliters, 0.574 Mole) and glycolic acid (0.156 Mole) were added, and the reactor was sealed under N$_2$. The reactor was pressurized to 250 psig (1.7 MPa) with H$_2$ and heated to 200° C. Upon reaching 200° C., the H$_2$ pressure was raised to 2000 psig (13.8 MPa). The autoclave was stirred and held at 200° C., 2000 psig (13.8 MPa) for a total of 3 hours. The autoclave was then cooled, excess gas vented and the contents recovered. The contents were analyzed by the use of an internal standard gas chromatography method to show the complete consumption of the glycolic acid and the formation of 0.154 moles of ethylene glycol, which corresponds to 100% conversion with a 99.2% selectivity to ethylene glycol.

The contents of the autoclave were vacuum stripped to a residue on a steam bath at 4 torr. The purpose of the distillation was to remove some of the product and to establish a base heel for reuse. The 27 milliliters of overhead product contained methanol and 0.068 mole of ethylene glycol. The heel from the distillation still contained ethylene glycol and was used in the next step.

The concentrated heel from the previous step was returned to the autoclave along with 0.10 grams of TRIPHOS to offset any handling and oxidation losses, 32 milliliters of methanol, and 0.156 mole of glycolic acid. The autoclave was subjected to the same reaction conditions as before. Analysis of the reaction product showed complete consumption of glycolic acid and the presence of 0.295 mole of ethylene glycol. The contents of the autoclave were subjected to the vacuum strip conditions again to yield 28.3 grams of overhead product containing 0.113 mole of ethylene glycol and a heel of less than 20 milliliters volume that was re-used in the next step.

The concentrated heel from the previous step was returned to the autoclave along with 0.10 grams of TRIPHOS to offset any handling and oxidation losses, 32 milliliters of methanol, and 0.156 mole of glycolic acid. The autoclave was subjected to the same reaction conditions as before. Analysis of the reaction product showed complete consumption of glycolic acid and the presence of 0.3623 mole of ethylene glycol. The reaction product was re-subjected to the vacuum strip procedure to yield 24.5 grams of overhead product containing 0.137 mole of ethylene glycol.

This series of runs demonstrate that the catalyst can be stripped of the product and that the catalyst-containing heel can be returned to the reactor for further use.

The invention has been described in detail with particular reference to preferred embodiments thereof, but it will be understood that variations and modifications can be effected within the spirit and scope of the invention.

We claim:

1. A process for preparing a 1,2-diol, which comprises contacting a 1,2-dioxygenated organic compound, with the exception of oxalic acid or ester thereof, with hydrogen, under hydrogenation conditions, in the presence of a catalyst composition comprising:
   (a) a ruthenium compound;
   (b) a trivalent phosphorus compound selected from 1,1,1-tris(diarylphosphinomethyl)alkyl or substituted alkyl; and
   (c) a promoter selected from Lewis acids, protic acids having an ionization constant (K$_i$) of $5 \times 10^{-3}$ or greater, onium salts, and mixtures thereof;
wherein said catalyst components (a)-(c) are dissolved in an organic solvent, to produce a 1,2-diol.

2. The process according to claim 1, wherein the 1,2-diol comprises ethylene glycol, 1,2-propylene glycol, 1,2-butanediol, or a mixture thereof.

3. The process according to claim 1, wherein the 1,2-dioxygenated organic compound comprises glyoxal, glycolic acid, glycol aldehyde, glycol aldehyde dimer, glycolic acid ester, methyl glycolate, oligomers of glycolic acid, oligomers of glycolic acid ester, lactic acid, lactic acid ester, oligomers of lactic acid, oligomers of lactic acid ester, 2-hydroxy butyric acid, esters of 2-hydroxy butyric acid, oligomers of 2-hydroxy butyric acid, or mixtures thereof.

4. The process according to claim 1, wherein the ruthenium compound is selected from ruthenium carboxylates, ruthenium acetylacetones, ruthenium hydride complexes, ruthenium carbonyl compounds, ruthenium halides, ruthenium oxides, ruthenium phosphine complexes, and mixtures thereof; and the trivalent phosphorus compound is selected from tris(diphenylphosphinomethyl)alkyl or substituted alkyl.

5. The process according to claim 4, wherein the ruthenium compound comprises ruthenium(III)acetylacetonate.

6. The process according to claim 1, wherein the trivalent phosphorus compound comprises 1,1,1-tris(diphenylphosphinomethyl)ethane.

7. The process according to claim 1, wherein the promoter is selected from ammonium hexafluorophosphate, tetrabutylammonium hexafluorophosphate, tetraphenylphosphonium bromide, sodium tetraphenyl borate, ammonium tetrafluoroborate, tetramethyl ammonium tetrafluoroborate, toluenesulfonic acid, phosphoric acid, triflic acid, sulfuric acid, methanesulfonic acid, trifluoroacetic acid, dodecylbenzenesulfonic acid, dinonylnaphthalenesulfonic acid, and mixtures thereof.

8. The process according to claim 7, wherein the promoter is selected from tetrabutylammonium hexafluorophosphate, triflic acid, toluenesulfonic acid, dodecylbenzenesulfonic acid, dinonylnaphthalenesulfonic acid, and mixtures thereof.

9. The process according to claim 1, wherein the organic solvent is selected from alcohols, ethers, hydrogenation starting materials, and hydrogenation reaction products.

10. The process according to claim 9, wherein the organic solvent is selected from methanol, ethanol, propanol, butanol, isobutanol, isopropanol, ethylene glycol, 1,2-propylene glycol, 1,3-propylene glycol, 2-methyl-1,3-propanediol, neopentyl glycol, 2-ethylhexanol, 1,4-butanediol, diethylene glycol, triethylene glycol, glycerol, hexanol, octanol, methoxy ethanol, diisopropyl ether, dipropyl ether, and mixtures thereof.

11. The process according to claim 10, wherein the organic solvent comprises methanol, ethylene glycol, 2-methyl-1,3-propanediol, 2-ethylhexanol, hexanol, octanol, or mixtures thereof.

12. The process according to claim 1, wherein said hydrogenation conditions comprise a temperature of 125° C. to 220° C., and a hydrogen pressure of 1500 psig to 3000 psig.

13. A process for preparing ethylene glycol, which comprises contacting glycolic acid or a derivative thereof with hydrogen, under hydrogenation conditions, in the presence of a catalyst composition comprising:
(a) ruthenium(III)acetylacetonate;
(b) 1,1,1-tris(diphenylphosphinomethyl)ethane; and
(c) a promoter selected from tetrabutylammonium hexafluorophosphate, triflic acid, toluenesulfonic acid, dodecylbenzenesulfonic acid, dinonylnaphthalenesulfonic acid, and mixtures thereof;
wherein said catalyst components (a)-(c) are dissolved in a solvent selected from methanol, ethylene glycol, 2-methyl-1, 3-propanediol, 2-ethylhexanol, hexanol, octanol, and mixtures thereof; to produce ethylene glycol.

14. The process according to claim 13, wherein said glycolic acid derivative is selected from methyl glycolate, oligomers of glycolic acid, and mixtures thereof.

15. The process according to claim 13, which further comprises separating the ethylene glycol from the catalyst components and recycling the catalyst components to the contacting step.

* * * * *